US011617510B2

(12) United States Patent
Samadani et al.

(10) Patent No.: US 11,617,510 B2
(45) Date of Patent: Apr. 4, 2023

(54) METHOD FOR DETECTING GLAUCOMA

(71) Applicants: Rosina Samadani, New York, NY (US); Thomas A. Castillo, Beaver Dam, WI (US)

(72) Inventors: Rosina Samadani, New York, NY (US); Thomas A. Castillo, Beaver Dam, WI (US)

(73) Assignee: Oculogica, Inc., New York, NY (US)

( * ) Notice: Subject to any disclaimer, the term of this patent is extended or adjusted under 35 U.S.C. 154(b) by 211 days.

(21) Appl. No.: 17/096,810

(22) Filed: Nov. 12, 2020

(65) Prior Publication Data

US 2021/0059524 A1 Mar. 4, 2021

Related U.S. Application Data

(63) Continuation of application No. 15/716,826, filed on Sep. 27, 2017, now Pat. No. 10,863,902.

(60) Provisional application No. 62/403,440, filed on Oct. 3, 2016.

(51) Int. Cl.
| | | |
|---|---|---|
| A61B 3/10 | (2006.01) | |
| A61B 3/14 | (2006.01) | |
| A61B 3/02 | (2006.01) | |
| A61B 3/00 | (2006.01) | |
| A61B 3/16 | (2006.01) | |
| A61B 3/113 | (2006.01) | |
| A61B 3/117 | (2006.01) | |

(52) U.S. Cl.
CPC .............. *A61B 3/16* (2013.01); *A61B 3/0025* (2013.01); *A61B 3/113* (2013.01); *A61B 3/117* (2013.01); *A61B 3/145* (2013.01); *G01N 2800/168* (2013.01)

(58) Field of Classification Search
CPC ........... A61B 3/103; A61B 3/14; A61B 3/113; A61B 3/1225; A61B 3/024; A61B 3/032; A61B 3/18; A61B 3/1015
USPC ................. 351/205, 206, 209–211, 221–223, 351/245–246
See application file for complete search history.

(56) References Cited

U.S. PATENT DOCUMENTS

| | | | | |
|---|---|---|---|---|
| 2001/0056359 | A1* | 12/2001 | Abreu ................. | A61B 5/4848 705/3 |
| 2013/0144185 | A1* | 6/2013 | Fuller ................. | A61B 5/7278 600/561 |
| 2013/0278899 | A1* | 10/2013 | Waldorf ............... | A61B 3/0091 351/209 |
| 2015/0190050 | A1* | 7/2015 | Samadani ............ | A61B 5/4076 600/558 |
| 2018/0279877 | A1* | 10/2018 | Berdahl ............... | A61B 3/1241 |

* cited by examiner

*Primary Examiner* — Dawayne Pinkney
(74) *Attorney, Agent, or Firm* — Wei & Sleman LLP (57) ABSTRACT

A method for assessing glaucoma in a patient may involve measuring an intraocular pressure of the patient and measuring an intracranial pressure in the patient, using a non-invasive eye tracking system. The method may then involve comparing the intraocular pressure to the intracranial pressure and assessing glaucoma in the patient, based on the comparing of the intraocular pressure to the intracranial pressure.

18 Claims, 4 Drawing Sheets

METHOD FOR DETECTING GLAUCOMA

CROSS-REFERENCE TO RELATED APPLICATIONS

This application is a continuation of U.S. patent application Ser. No. 15/716,826, filed Sep. 27, 2017, entitled "Method for Detecting Glaucoma," and claims the benefit of U.S. Provisional Patent Application No. 62/403,440, filed Oct. 3, 2016, entitled, "Method for Detecting Glaucoma." The disclosures of these applications are hereby incorporated by reference in their entirety into the present application as if fully set forth herein.

This application also incorporates by reference U.S. Pat. No. 9,642,522 and U.S. Patent Application Pub. Nos. 2016/0278716 and 2017/0172408, which will be referred to below as "The Incorporated References." All publications, patent applications, patents and other reference material mentioned in this application are hereby incorporated by reference in their entirety.

TECHNICAL FIELD

This application is directed to medical devices, systems and methods. More specifically, the application is directed to devices, systems and methods for diagnosing glaucoma.

BACKGROUND OF THE INVENTION

Glaucoma is a disease that damages the optic nerve and can lead to blindness. It usually occurs when fluid builds up in the front part of the eye, thus increasing pressure in the eye and damaging the optic nerve. Glaucoma is one of the leading causes of blindness in the United States and throughout the world, and vision loss due to glaucoma cannot be recovered. Unfortunately, the most common form of glaucoma has no warning signs, and the effect is so gradual that patients often notice no change in vision until the condition reaches an advanced stage.

Early detection of glaucoma is critical for protecting a patient's vision. At the same time, however, glaucoma can sometimes be challenging to diagnose. An ideal eye exam to test for glaucoma includes five tests: (1) tonometry; (2) ophthalmoscopy; (3) perimetry; (4) gonioscopy; and (5) pachymetry. Tonometry measures the pressure within your eye. During tonometry, eye drops are used to numb the eye. Then a doctor or technician uses a device called a tonometer to measure the inner pressure of the eye. A small amount of pressure is applied to the eye by a tiny device or by a warm puff of air. Ophthalmoscopy involves the doctor examining your optic nerve with an ophthalmoscope for glaucoma damage. Eye drops are used to dilate the pupil so that the doctor can see through your eye to examine the shape and color of the optic nerve. Perimetry is a visual field test that produces a map of the patient's complete field of vision. Gonioscopy is an exam that helps determine whether the angle where the iris meets the cornea is open and wide or narrow and closed. During the exam, eye drops are used to numb the eye. A hand-held contact lens is gently placed on the eye. This contact lens has a mirror that shows the doctor if the angle between the iris and cornea is closed and blocked (a possible sign of angle-closure or acute glaucoma) or wide and open (a possible sign of open-angle, chronic glaucoma). Pachymetry is a simple test to measure the thickness of the cornea. A probe called a pachymeter is gently placed on the front of the eye (the cornea) to measure its thickness.

Although this combination of tests is relatively effective at diagnosing glaucoma, it would be advantageous to have alternative systems and methods for diagnosing and/or detecting the risk for glaucoma.

BRIEF SUMMARY

A growing body of evidence supports the idea that glaucoma is not a disease of intraocular pressure (TOP) alone, but instead corresponds more directly to the differential between IOP and cerebrospinal fluid (CSF) pressure. Elevated IOP, by itself, may explain primary open-angle glaucoma, but it cannot account for normotension or low-tension glaucoma. Nor can clinicians explain why elevated IOP may not lead to glaucoma in ocular hypertensives. Unfortunately, however, there are no currently available tests for measuring CSF pressure.

The methods and systems described herein involve noninvasively measuring intracranial pressure (ICP), measuring IOP, determining the difference between the two, and diagnosing glaucoma based on the difference. ICP is related to, and may be used as a proxy for, CSF pressure. This two-pressure method of detecting glaucoma (determining the IOP vs. ICP differential) may be a more effective method for detecting and diagnosing glaucoma than only looking at IOP. When IOP is greater than ICP (regardless of whether the ICP is normal or abnormal), glaucoma can occur. The difference between IOP and ICP is likely more important than the absolute pressure values. IOP higher than ICP results in posterior cupping that is seen in glaucoma. In normotension glaucoma, there is normal IOP but a low ICP. The two-pressure model also explains ocular hypertension without glaucoma, because these individuals have elevated IOP with a similarly elevated ICP that protects the optic nerve. Even though the absolute pressure on both sides of the lamina cribrosa is high, the normal pressure gradient allows for normal axonal transport.

In one aspect of the present application, a method for assessing glaucoma in a patient involves: measuring an intraocular pressure of the patient; measuring an intracranial pressure in the patient, using a noninvasive eye tracking system; comparing the intraocular pressure to the intracranial pressure; and assessing glaucoma in the patient, based on the comparing of the intraocular pressure to the intracranial pressure. "Assessing the glaucoma," may involve, but is not limited to, diagnosing, detecting, monitoring and/or assessing a risk of glaucoma in the patient. In some embodiments, the intraocular pressure is measured using a non-contact measurement method.

In some embodiments, comparing the intraocular pressure to the intracranial pressure involves determining whether a ratio of the intraocular pressure to the intracranial pressure represents a high risk, a low risk or no risk of glaucoma. In some embodiments, measuring the intracranial pressure involves: showing a video to the patient on a stimulus screen of the eye tracking system, where the video moves across the stimulus screen; tracking movement of the patient's eyes, using an eye tracking camera of the eye tracking system; assessing an ability of the patient's eyes to track the video; and determining the intracranial pressure from the ability of the patient's eyes to track the video, using a processor of the eye tracking system. In some embodiments, comparing the intraocular pressure to the intracranial pressure may involves: determining, with a processor of the eye tracking system, whether the measured intraocular pressure is high, normal or low; determining, with the processor, whether the measured intracranial pressure is high, normal or low;

comparing, with the processor, the two determinations of high, normal or low; and assessing, with the processor, a glaucoma risk in the patient, based on the comparison of the two determinations.

In another aspect of the present application, a system for assessing glaucoma in a patient may include an intraocular pressure measurement device, a noninvasive, eye-tracking, intracranial pressure measurement system, and a processor coupled with the intraocular pressure measurement device and the intracranial pressure measurement device for comparing a measured intraocular pressure with a measured intracranial pressure and assessing glaucoma in the patient based at least in part on the comparison. In some embodiments, the processor is configured to determine a ratio of the intraocular pressure to the intracranial pressure and is also configured to determine whether the ratio represents a high risk, a low risk or no risk of glaucoma. In some embodiments, the processor is configured to compare the intraocular pressure to the intracranial pressure by determining whether a ratio of the intraocular pressure to the intracranial pressure represents a high risk, a low risk or no risk of glaucoma. In some embodiments, the intracranial pressure measurement system is configured to perform a method, such as the one described immediately above.

These and other aspects and embodiments are described in greater detail below, in reference to the attached drawing figures.

DETAILED DESCRIPTION OF THE INVENTION

The assignee of the present patent application has developed eye tracking devices, systems and methods that may be used to track the movement of a patient's pupils over time as they follow a video moving across a screen and measure metrics such as distance traveled over time and the ability to coordinate eye movements. Cranial Nerve III and VI palsies, for example, may be identified using this system and method, which includes at least one computer processor that employs an algorithm to perform diagnostic calculations. These devices, systems and methods are described more fully in The Incorporated References. The present application uses the same technology, method and algorithm to provide a non-invasive eye-tracking methodology to measure ICP, and then compares that measured ICP with IOP to assess the risk of glaucoma in the patient.

In one embodiment, IOP is measured via non-contact tonometry and is compared with ICP measured via the non-invasive methods and systems described in The Incorporate References. In alternative embodiments, IOP may be measured using any other suitable methods, and ICP may be determined from other eye tracking methods. In some embodiments, an eye tracking system or device may be incorporated into a tonometry system or device. Alternatively, a tonometry device may be incorporated into an eye tracking system. Any combination of IOP determination devices and methods and eye tracking devices and methods may be made, without departing from the scope of the invention.

Figure 1:
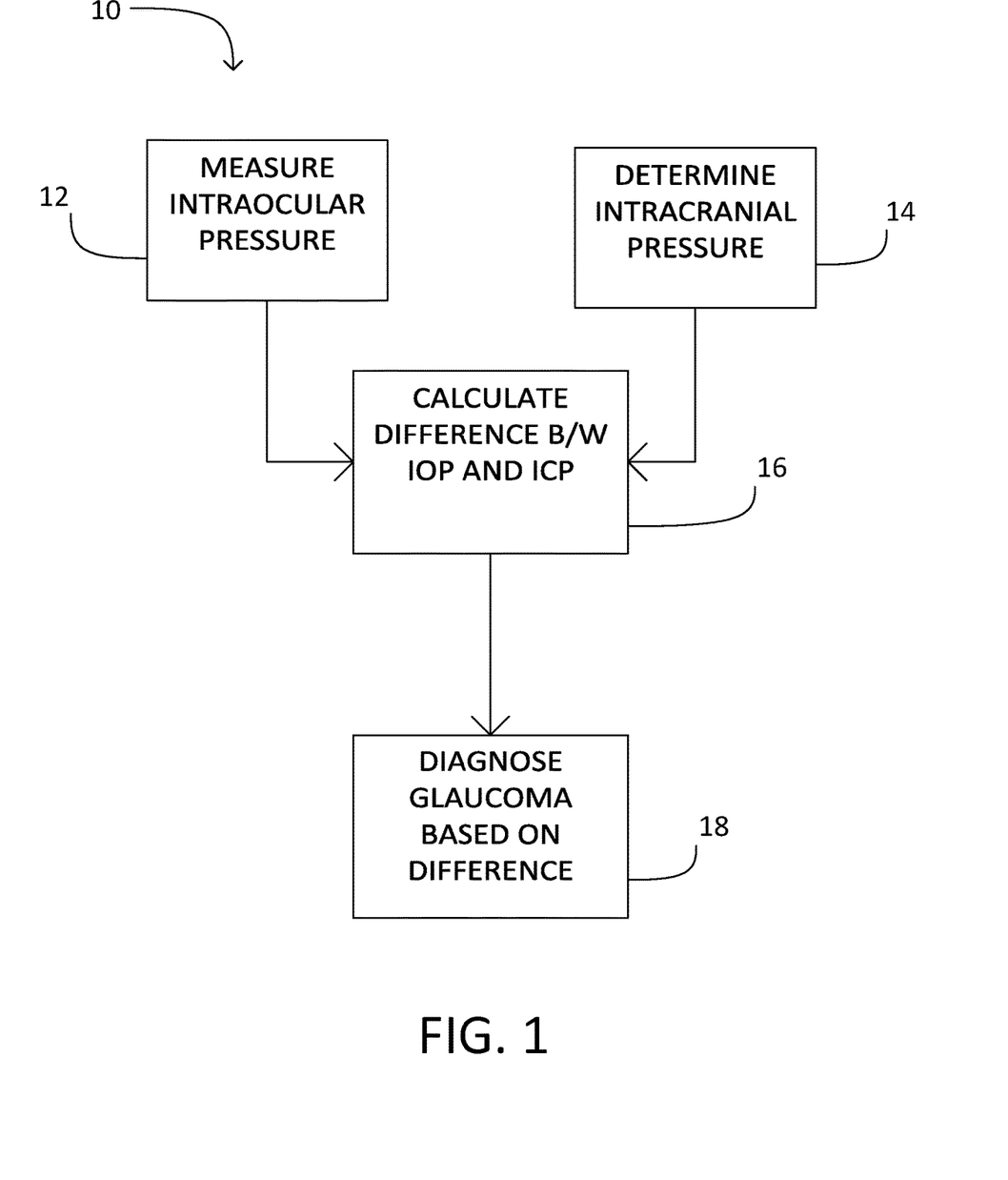
FIG. 1 is a flow chart illustrating a method for using ICP and IOP to assess whether a patient has glaucoma or what the patient's risk of glaucoma is, according to one embodiment.

Referring to FIG. 1, a method 10 is outlined for assessing glaucoma risk and/or diagnosing glaucoma in a patient. In this method 10, IOP is measured 12 using any suitable, non-invasive measurement technique. ICP is measured 14 using eye tracking, as described in The Incorporated References. These two method steps 12, 14 may be performed in any order. In the next step, a difference between IOP and ICP is calculated 16. This calculated difference is then used to assess glaucoma risk and/or diagnose glaucoma in the patient 18.

Table 1, immediately below, is an example embodiment of how ICP and IOP are compared, to help assess glaucoma risk. This comparison may be made, and glaucoma risk may be assessed, using an algorithm in a computer processor of the eye tracking system.

TABLE 1

| | ICP | | |
|---|---|---|---|
| IOP | Low | Normal | High |
| Low | Lower risk | Lower risk | Lower risk |
| Normal | Higher risk | Lower risk | Lower risk |
| High | Higher risk | Higher risk | Lower risk |

In some embodiments, parameters measured via the methods and systems of The Incorporated References may also be used to determine lower ICP relative to IOP. A comparator based on IOP and ICP as follows screens for glaucoma risk:

TABLE 2

| | ICP | | |
|---|---|---|---|
| IOP | Low | Normal | High |
| Low | Lower risk | Lower risk | Lower risk |
| Normal | Higher risk (NT; Group L) | Lower risk (Group C) | Lower risk |
| High | Higher risk (POAG; Group P) | Higher risk (POAG; Group P) | Lower risk (No glaucoma, Group I) |

For the following study the 4 patient groups under consideration are:

TABLE 3

| | Assumed ICP: | | |
|---|---|---|---|
| IOP | Low | Normal | High |
| Low Normal | Lower risk Group L: Normotensive glaucoma | Lower risk Group C: Normals | Lower risk Lower risk |
| High | Group P: POAG | Group P: POAG | Group I: No glaucoma but high IOP |

In some embodiments, eye-tracking may be used to identify normotensive glaucoma patients by detecting low ICP in patients with a normal tonometry test. Normotensive glaucoma patients present with abnormal eye-tracking results indicative of abnormal ICP but normal tonometry results. Alternatively, primary open-angle glaucoma (POAG) patients present with abnormal eye-tracking and abnormal tonometry results. The differential between ICP (as measured by eye-tracking) and IOP (as measured by tonometry) can be used as an additional indicator for glaucoma.

| | Patient: | | |
|---|---|---|---|
| Test: | Normal | POAG | LT/NT Glc |
| Panchymetry | Normal | Abnormal | Abnormal |
| Optic Nerve | Normal | Abnormal | Abnormal |
| Visual Field | Normal | Abnormal | Abnormal |
| Tonometry (IOP) | Normal | Abnormal | Normal |
| Eye-tracking (ICP) | Normal | Abnormal (high) | Abnormal (low) |

In addition, eye-tracking may explain why some patients with high IOP do not have glaucoma, by detecting high ICP in patients with abnormal tonometry tests. Individuals with elevated IOP with a similarly elevated ICP that protects the optic nerve do not develop glaucoma. Even though the absolute pressure on both sides of the lamina cribrosa is high, the normal pressure gradient allows for normal axonal transport.

| | Patient: | | |
|---|---|---|---|
| Test: | Normal IOP | Elevated IOP with glaucoma | Elevated IOP but no glaucoma |
| Panchymetry | Normal | Abnormal | Normal |
| Optic Nerve | Normal | Abnormal | Normal |
| Visual Field | Normal | Abnormal | Normal |
| Tonometry (IOP) | Normal | Abnormal | Abnormal |
| Eye-tracking (ICP) | Normal | Abnormal | Abnormal |

For ICP, values≤12 mmHg are generally considered normal, and ICP values>12 mmHg are generally considered to be elevated. For TOP, values≥22 are considered to be high. Patients with TOP below that at the time of diagnosis (e.g., before treatment) are called normal tension or low tension glaucoma. Those with elevated TOP are called primary open-angle glaucoma. The following eye-tracking parameters may be used to identify low tension or normo-tension glaucoma:

Example Parameters:

| | |
|---|---|
| right.distLef | Right eye, Right segment mean length of visual path recording |
| right.distBot | Right eye, bottom segment mean length of visual path recording |
| left.varXlef | Left eye, mean variance of X direction along the left side of the visual path recording |
| right.skewLef | Right eye, mean difference between mean and median along the Right side of the visual path recording |
| left.skewLef | Left eye, mean difference between mean and median along the left side of the visual path recording |
| right.varXlef | Right eye, mean variance of X direction along the Right side of the visual path recording |
| left.skewTop | Left eye, mean difference between mean and median along the top side of the visual path recording |
| right.widthmean | Right eye, mean width of visual path recording (Right minus right) |
| right.widthmedian | Right eye, median width of visual path recording (Right minus right) |
| right.areamean | Right eye, mean value of width*height, averaged over 5 cycles of visual path recording |
| conj.velRit | Total difference between Left and Right eye velocity along the right segment of the visual path recording |
| left.areamean | Left eye, mean value of width*height, averaged over 5 cycles of visual path recording |
| left.skewTopNorm | Left eye, mean normalized difference between mean and median along the top side of the visual path recording |

By measuring the effects of elevated ICP in patients who have elevated IOP, the method may also be used to differentiate patents who have a large differential from those who have a small differential in pressures. The latter are typically at a lower risk for regular glaucoma. The former are typically at a higher risk.

Figure 2:
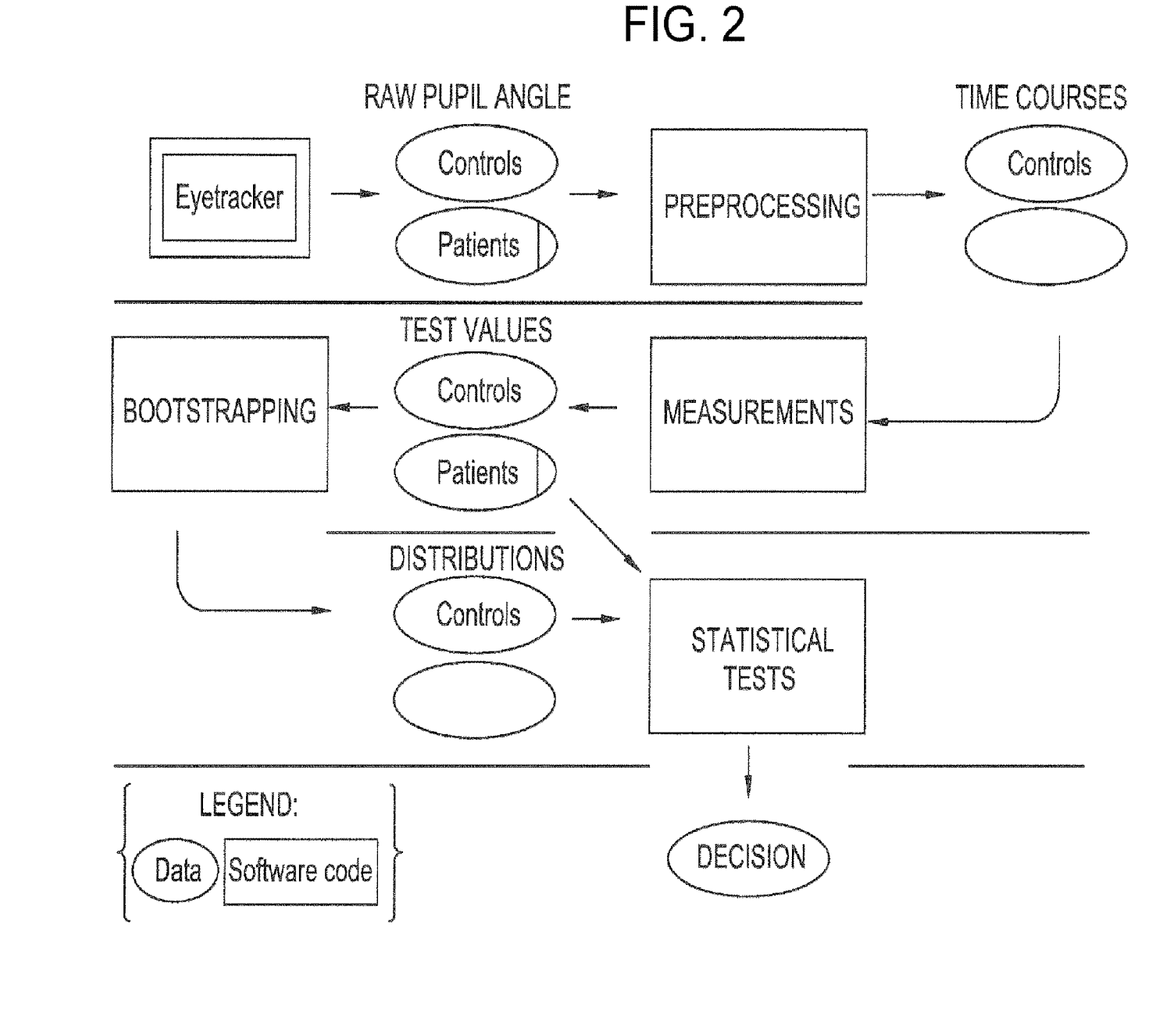
FIG. 2 is a flowchart demonstrating how eye movement tracking of patients and controls may be tested and compared, according to one embodiment.
Figure 3:
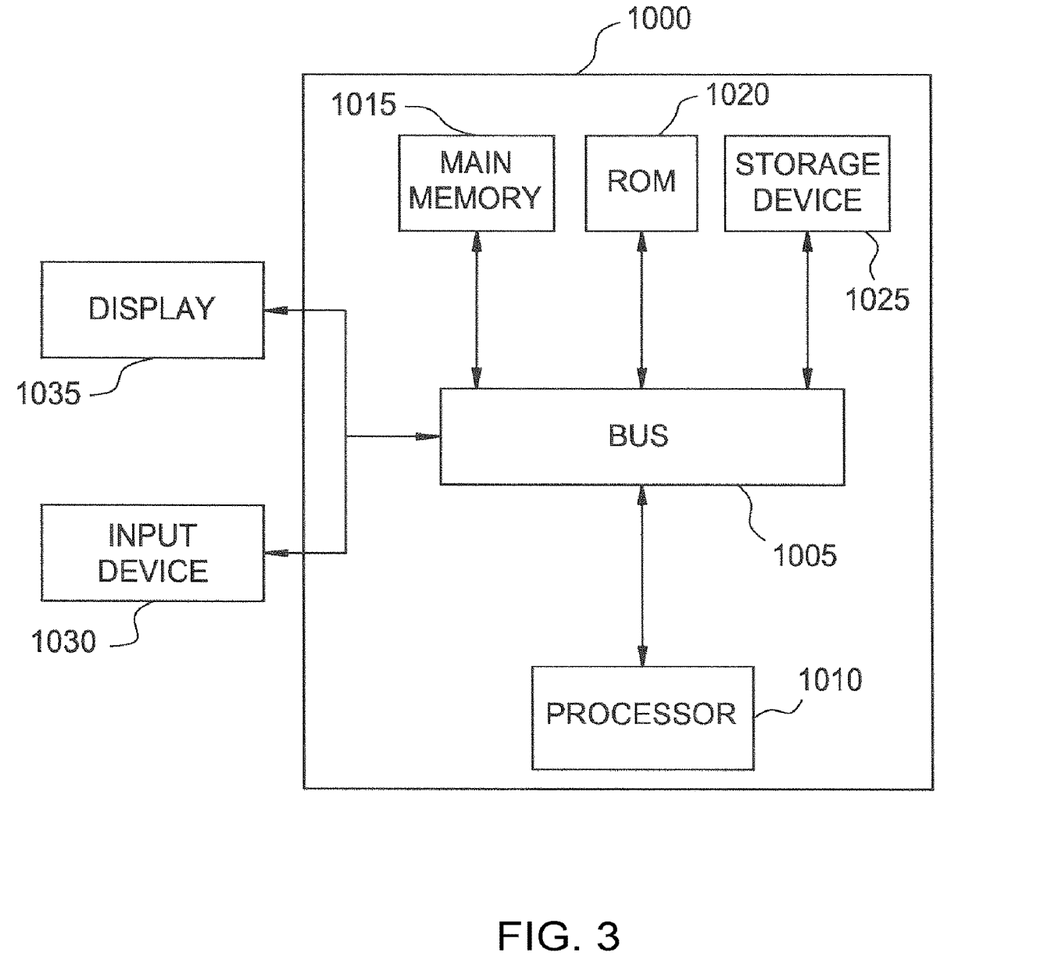
FIG. 3 is a block diagram of a computer system for use in the system and method described herein, according to one embodiment.
Figure 4:
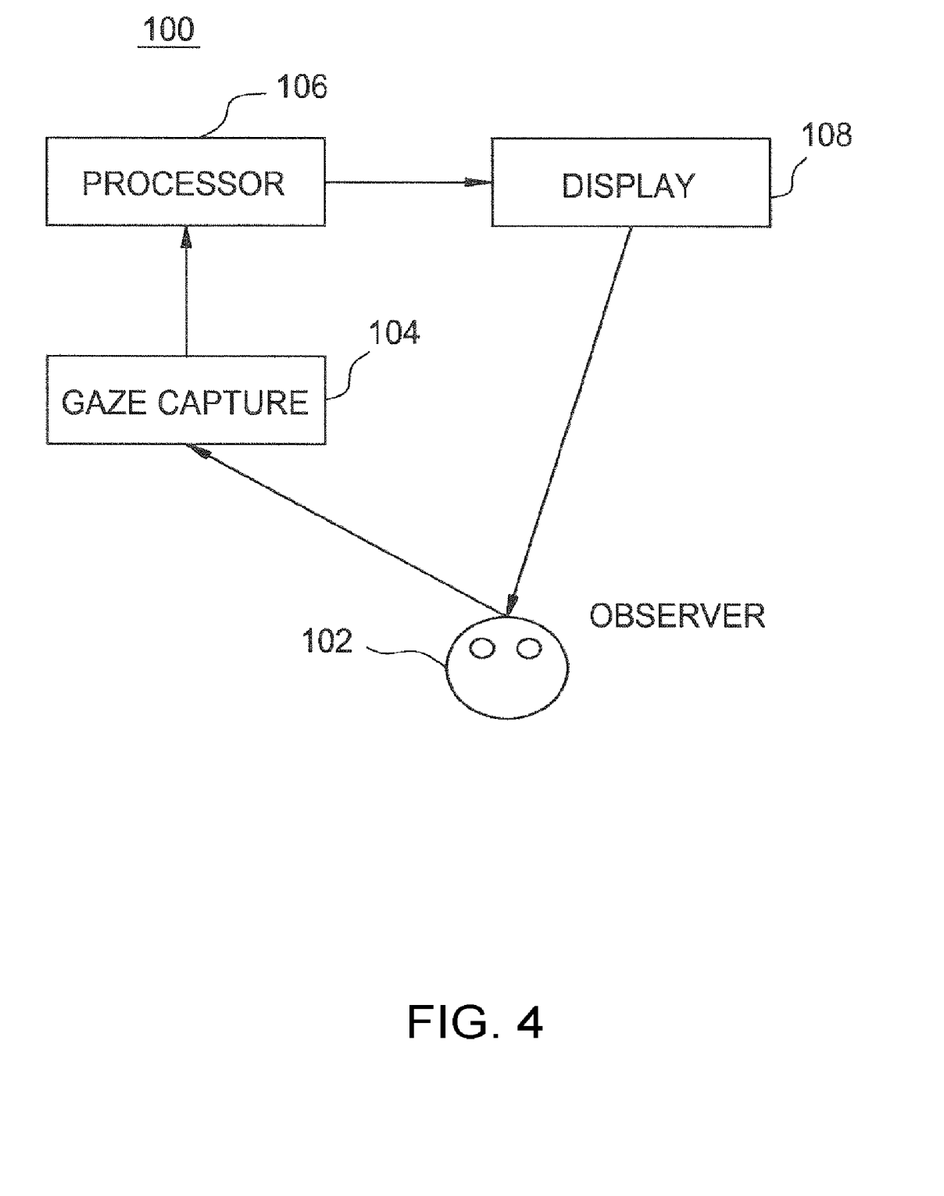
FIG. 4 is a schematic diagram showing a configuration of how a subject's eye movements are measured, analyzed and displayed by the computer system of FIG. 18, according to one embodiment.

A computing system according to one embodiment and described in The Incorporated references is described in FIGS. 2-4. Implementations of the observer matter and the functional operations described herein can be implemented in other types of digital electronic circuitry, or in computer software, firmware, or hardware, including the structures disclosed in this specification and their structural equivalents, or in combinations of one or more of them. The computer system or computing device 1000 can be used to implement a device that includes the processor 106 and the display 108, the eye movement/gaze tracker component 104, etc. The computing system 1000 includes a bus 1005 or other communication component for communicating information and a processor 1010 or processing circuit coupled to the bus 1005 for processing information. The computing system 1000 can also include one or more processors 1010 or processing circuits coupled to the bus for processing information. The computing system 1000 also includes main memory 1015, such as a random access memory (RAM) or other dynamic storage device, coupled to the bus 1005 for storing information, and instructions to be executed by the processor 1010. Main memory 1015 can also be used for storing position information, temporary variables, or other intermediate information during execution of instructions by the processor 1010. The computing system 1000 may further include a read only memory (ROM) 1010 or other static storage device coupled to the bus 1005 for storing static information and instructions for the processor 1010. A storage device 1025, such as a solid state device, magnetic disk or optical disk, is coupled to the bus 1005 for persistently storing information and instructions.

The computing system 1000 may be coupled via the bus 1005 to a display 1035, such as a liquid crystal display, or active matrix display, for displaying information to a user. An input device 1030, such as a keyboard including alphanumeric and other keys, may be coupled to the bus 1005 for communicating information and command selections to the processor 1010. In another implementation, the input device 1030 has a touch screen display 1035. The input device 1030 can include a cursor control, such as a mouse, a trackball, or cursor direction keys, for communicating direction information and command selections to the processor 1010 and for controlling cursor movement on the display 1035.

According to various implementations, the processes described herein can be implemented by the computing system 1000 in response to the processor 1010 executing an arrangement of instructions contained in main memory 1015. Such instructions can be read into main memory 1015 from another computer-readable medium, such as the storage device 1025. Execution of the arrangement of instructions contained in main memory 1015 causes the computing system 1000 to perform the illustrative processes described herein. One or more processors in a multi-processing arrangement may also be employed to execute the instructions contained in main memory 1015. In alternative implementations, hard-wired circuitry may be used in place of or in combination with software instructions to effect illustrative implementations. Thus, implementations are not limited to any specific combination of hardware circuitry and software.

Implementations of the observer matter and the operations described herein can be implemented in digital electronic circuitry, or in computer software, firmware, or hardware, including the structures disclosed in this specification and their structural equivalents, or in combinations of one or more of them. The observer matter described herein can be implemented as one or more computer programs, i.e., one or more modules of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described herein can be performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the observer matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Described herein are many specific implementation details, these should not be construed as limitations on the scope of any inventions or of what may be claimed, but rather as descriptions of features specific to particular implementations of particular inventions. Certain features described herein in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated in a single software product or packaged into multiple software products.

The relationship of aspect ratio and variance as measures of the signal. When the (x,y) pairs are plotted to show the 'box plots,' they have been preprocessed because the absolute values of the raw data are of limited use since changes in the signal over time are most important. There are many ways to normalize data, including dividing by the mean, by the standard deviation, or by the variance. Furthermore, the standard deviation or variance can be computed for all the data at once or x can be normalized using the variance of x and y can be normalized using the variance of y. Any normalization procedure for periodic data likely includes subtracting the mean, so the signal can be plotted as signal change alternating around zero. All of these transformations are conventional and widely used in data analysis by those of ordinary skill in the art. The details depend on the question being asked and the type of modeling or statistical testing being used.

In creating the box plots described herein, the raw data is preprocessed as follows: for the x (horizontal) and y (vertical) vectors independently, the mean is subtracted and divided by the standard deviation (which is the square root of the variance). This puts all the data in the same relative frame (zero-mean, max and min about 1 and −1). This is the reason the boxes look square (even if the stimulus presentation monitor is not square).

This means that 'long' and 'short' sides are reflecting relative variability. If the variability is high, the denominator is high and the measure value low. So, for example, if the variability of the horizontal (x) data is high relative to the variability of the vertical (y) data, the horizontal aspect of the box will be relatively smaller, and the result will be a tall skinny box (higher aspect ratio). Conversely, if the variability of the vertical (y) data is high relative to the variability of the horizontal (x) data, the vertical range will be reduced and the result will be a short fat box (lower aspect ratio).

The foregoing is believed to be a complete and accurate description of various embodiments of a system and method for assessing glaucoma in a patient. The description is of embodiments only, however, and is not meant to limit the scope of the invention set forth in the claims.

We claim:

1. A method for assessing glaucoma in a patient, the method comprising:
    obtaining an intraocular pressure of the patient;
    measuring an intracranial pressure in the patient using a non-contacting eye tracking system having an eye movement tracking camera, the eye movement tracking camera being spaced from the patient;
    comparing the intraocular pressure to the intracranial pressure; and
    assessing glaucoma in the patient, based on the comparing of the intraocular pressure to the intracranial pressure.

2. The method of claim 1, wherein assessing the glaucoma comprises at least one of diagnosing, detecting, monitoring or assessing a risk of glaucoma in the patient.

3. The method of claim 1, wherein obtaining the intraocular pressure comprises using a non-contact measurement method.

4. The method of claim 1, wherein obtaining the intraocular pressure comprises using a tonometry device, and wherein the noninvasive eye tracking system is combined with the tonometry device.

5. The method of claim 1, wherein obtaining the intraocular pressure comprises using a tonometry device incorporated into the noninvasive eye tracking system.

6. The method of claim 1, wherein comparing the intraocular pressure to the intracranial pressure comprises determining whether a ratio of the intraocular pressure to the intracranial pressure represents a high risk, a low risk or no risk of glaucoma.

7. The method of claim 1, wherein measuring the intracranial pressure comprises:
    showing a video to the patient on a stimulus screen of the eye tracking system, wherein the video moves across the stimulus screen;
    tracking movement of the patient's eyes, using an eye tracking camera of the eye tracking system;
    assessing an ability of the patient's eyes to track the video; and
    determining the intracranial pressure from the ability of the patient's eyes to track the video, using a processor of the eye tracking system.

8. The method of claim 1, wherein comparing the intraocular pressure to the intracranial pressure comprises:
    determining, with a processor of the eye tracking system, whether the measured intraocular pressure is high, normal or low;
    determining, with the processor, whether the measured intracranial pressure is high, normal or low;
    comparing, with the processor, the two determinations of high, normal or low; and
    assessing, with the processor, a glaucoma risk in the patient, based on the comparison of the two determinations.

9. A system for assessing glaucoma in a patient, the system comprising:
    an intraocular pressure measurement device;
    a non-contacting, eye tracking measurement device having an eye movement tracking camera; and
    a processor coupled with the intraocular pressure measurement device and the eye tracking measurement device, wherein the processor is configured to:
    calculate an intracranial pressure of the patient, based on a measurement of eye tracking of the patient measuring with the eye movement tracking camera;
    compare a measured intraocular pressure of the patient with the calculated intracranial pressure; and
    assess glaucoma in the patient based at least in part on the comparison of the intraocular pressure with the intracranial pressure.

10. The system of claim 9, wherein assessing the glaucoma comprises at least one of diagnosing, detecting, monitoring or assessing a risk of glaucoma in the patient.

11. The system of claim 9, wherein the intraocular pressure measurement device comprises a non-contact measurement device.

12. The system of claim 9, wherein intraocular pressure measurement device comprises a tonometry device.

13. The system of claim 12, wherein the eye tracking measurement device is combined with the tonometry device.

14. The system of claim 12, wherein the tonometry device is incorporated into the eye tracking measurement device.

15. The system of claim 9, wherein the processor is further configured to:
   determine a ratio of the intraocular pressure to the intracranial pressure; and
   determine whether the ratio represents a high risk, a low risk or no risk of glaucoma.

16. The system of claim 9, wherein the processor is configured to compare the intraocular pressure to the intracranial pressure by determining whether a ratio of the intraocular pressure to the intracranial pressure represents a high risk, a low risk or no risk of glaucoma.

17. The system of claim 9, wherein the eye tracking measurement device is configured to perform a method, comprising:
   showing a video to the patient on a stimulus screen, wherein the video moves across the stimulus screen;
   tracking movement of the patient's eyes, using an eye tracking camera;
   assessing an ability of the patient's eyes to track the video; and
   determining the intracranial pressure from the ability of the patient's eyes to track the video, using the processor.

18. The system of claim 9, wherein comparing the intraocular pressure to the intracranial pressure comprises:
   determining, with the processor, whether the measured intraocular pressure is high, normal or low;
   determining, with the processor, whether the measured intracranial pressure is high, normal or low;
   comparing, with the processor, the two determinations of high, normal or low; and
   assessing, with the processor, a glaucoma risk in the patient, based on the comparison of the two determinations.

* * * * *